July 19, 1932. L. BURBANK Plant Pat. 18
PLUM
Filed Dec. 23, 1930
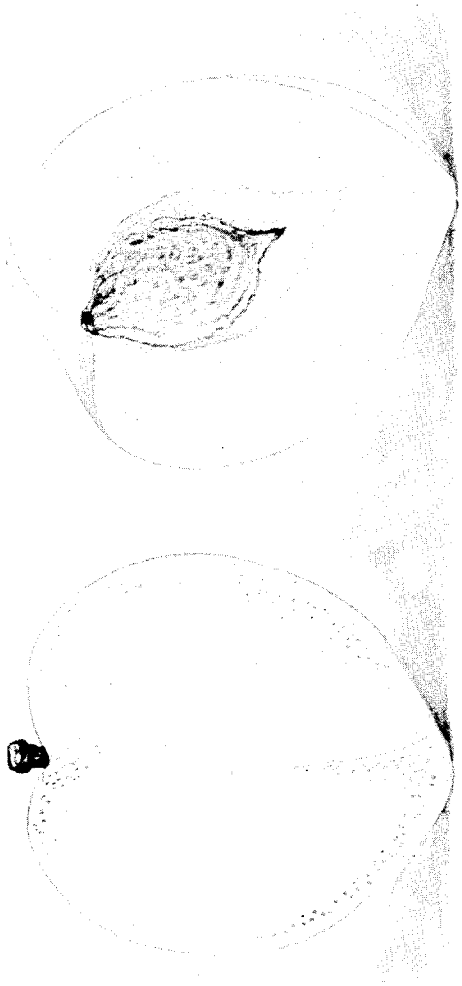
Elizabeth Waters Burbank, Executrix of
Luther Burbank, Deceased.
Robb & Robb
Attorneys Patented July 19, 1932

Plant Pat. 18

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S. NURSERIES & ORCHARDS COMPANY, OF LOUISIANA, MISSOURI

PLUM

Application filed December 23, 1930. Serial No. 504,400.

This invention relates to a new and distinct variety of plum.

One of the important objects in the creation of the present variety was to overcome the very objectionable features of the commonly known plum, residing in the watery and stringy character of these old plums. This soft, watery characteristic of the meat in the previous fruit materially interfered with its shipment to distances and reduced its keeping qualities to such an extent as to limit its marketability to a marked degree. Furthermore, as well known, the flesh adhered to the stone in an objectionable manner.

Thus it was the important purpose to produce a plum having a greater freestone characteristic, and a flesh which was firm and apricot-like, as well as sweeter in taste with higher flavors.

Not only has this present plum the foregoing desirable characteristics, but it proved to be larger in size with brighter colored skin and on the whole the trees are more regular bearing.

The attached drawing and specification show the distinctions and characteristics of the new variety of plum which has been asexually reproduced.

*Tree*

The growth of the tree is moderately vigorous. It is quite bushy, with stiff upright branches, presenting a rather open head. The forks are very acute, being about fifteen to twenty degrees from the vertical. The older bark is rough and not readily exfoliating, possessing in appearance rather a weathered surface.

*Fruit*

*Form.*—The form of the fruit is cordate, with unequal sides but not ill shaped. The size is very large, being about two and one-half inches on the average in axial diameter, about two and three-eighths inches in the longest transverse diameter and two and one-half inches in the shortest diameter. The stem is short, about three-eighths inch in length; is stout, and has a small area of attachment to the fruit for the size of plum, and is brown in color. The cavity is rather small, narrow, shallow, and acute. The suture begins at the stem, is deep and distinctly marked, extending to the apex which is prominent, with a pistil scar slightly beyond the apex. The surface is smooth and glossy.

*Color.*—The color is golden, faintly mottled under transparent skin, with numerous submerged minute greenish dots, almost transparent in character. The veinings show as light orange yellow, the translucent areas as deep chrome yellow.

The bloom is heavy, white, and easily removed, the surface becoming waxy.

*Skin.*—The skin is moderately thick and tough, adhering to the flesh, a distinctively advantageous feature.

*Stone.*—The stone is ovate with an acuminate brown point. It is small in proportion to the size of the fruit, being about one and three-eighths inches long, three-quarters inch wide and one-half inch thick. The ventral suture presents a sharp edge, almost winged, flanked by broken ridges and furrows, marked by depressions relating to fibers originating in the pit. The dorsal suture is a broken furrow, distinctly marked with depressions or pockets as above described. The sides of the stone are minutely pitted and ridged at both base and point. The stone's color is a warm buff with brownish shadings. The pit cavity is open and larger than the stone, which is entirely free.

*Flesh.*—The flesh is rather firm as enclosed by the skin, but very tender and melting when cut and eaten. The juice is abundant with faint amber yellow tinge. The flesh color is deep chrome yellow, somewhat translucent, uniform from skin to pit cavity. The quality is excellent.

(The colors are in accordance with Ridgway's color standard.)

The specification herewith manifest the general characteristics of the plum, yet it is understood that they may vary slightly due to cultivation and environment.

What is claimed as new is:

The new and distinct variety of plum tree characterized particularly by the chrome yellow color and firmness of the flesh of its fruit as herein shown and described.

In testimony whereof I affix my signature.

ELIZABETH WATERS BURBANK,
*Executrix of Luther Burbank, Deceased.*